United States Patent [19]

Peck et al.

[11] Patent Number: 5,703,104
[45] Date of Patent: Dec. 30, 1997

[54] CYCLIC AMIDES AND DERIVATIVES THEREOF

[75] Inventors: James V. Peck; Gevork Minaskanian, both of Richmond; Mark C. Sleevi, Midlothian, all of Va.

[73] Assignee: Durham Pharmaceuticals LLC, Durham, N.C.

[21] Appl. No.: 674,843

[22] Filed: Jul. 3, 1996

Related U.S. Application Data

[60] Provisional application No. 60/001,162, Jul. 14, 1995 and 60/000,947, Jul. 7, 1995.

[51] Int. Cl.$^6$ .................. A61K 31/41; A61K 31/40; C07D 277/04; C07D 263/04
[52] U.S. Cl. .................. 514/369; 514/392; 514/380; 514/423; 514/424; 548/183; 548/223; 548/318.5; 548/544; 548/545
[58] Field of Search .................. 548/183, 227, 548/318.5, 544, 545; 514/369, 392, 380, 423, 424

[56] References Cited

U.S. PATENT DOCUMENTS

| | | | |
|---|---|---|---|
| 3,100,180 | 8/1963 | Smith et al. | 167/91 |
| 3,989,815 | 11/1976 | Rajadhyaksha | 424/60 |
| 3,989,816 | 11/1976 | Rajadhyaksha | 424/60 |
| 3,991,203 | 11/1976 | Rajadhyaksha | 424/274 |
| 4,122,170 | 10/1978 | Rajadhyaksha | 424/180 |
| 4,316,893 | 2/1982 | Rajadhyaksha | 424/180 |
| 4,405,616 | 9/1983 | Rajadhyaksha | 424/244 |
| 4,415,563 | 11/1983 | Rajadhyaksha | 424/244 |
| 4,423,040 | 12/1983 | Rajadhyaksha | 424/180 |
| 4,424,210 | 1/1984 | Rajadhyaksha | 424/180 |
| 4,444,762 | 4/1984 | Rajadhyaksha | 424/180 |
| 4,960,771 | 10/1990 | Rajadhyaksha | 514/228.8 |
| 5,091,379 | 2/1992 | Aungst | 514/159 |

OTHER PUBLICATIONS

Brain, K. et al., "Electrostatic Factors in the Activity of Penetration Enhancers," *abstract of presentations at the Third International Prediction of Percutaneous Penetration Conference*, p. C5 (1993).

*Primary Examiner*—Robert T. Bond
*Attorney, Agent, or Firm*—Sterne, Kessler, Goldstein & Fox, P.L.L.C.

[57] ABSTRACT

Compounds, topical compositions and methods useful for preventing the penetration of toxic chemicals through the skin of a mammal are disclosed.

The compounds of the invention provide an enhanced barrier for the skin of a mammal to further inhibit or decrease the passage of bioactive agents through the skin of a mammal either from the outside environment into the systems of said mammal or from the mammal into the outside environment.

9 Claims, No Drawings

CYCLIC AMIDES AND DERIVATIVES THEREOF

This application claims the benefit under 35 U.S.C. §119(e)(1) of earlier-filed provisional patent applications, Appl. No. 60/001,162, filed Jul. 14, 1995, abn and Appl. No. 60/000,947, filed Jul. 7, 1995, abn. The contents of each of these provisional applications is fully incorporated by reference herein.

BACKGROUND OF THE INVENTION

1. Field of the Invention

The invention relates to novel compounds that inhibit the penetration of toxic chemicals and bioactive agents across the stratum corneum. The compounds are useful for applying to the skin of a mammal to inhibit or decrease the passage of toxic chemicals and other bioactive agents from the outside environment into the body, e.g., the bloodstream, or from the body into the outside environment.

2. Related Art

It is well known that the skin is an effective barrier against the penetration of many chemical agents. The epidermis of the skin has an exterior layer of dead cells called the stratum corneum which is tightly compacted and oily and which provides an effective barrier against gaseous, solid or liquid chemical agents, whether used alone or in water or oil solutions. If an agent penetrates the stratum corneum, it can readily pass through the basal layer of the epidermis and into the dermis. If the agent is a harmful one, for example a toxic chemical, penetration through the stratum corneum is an event to be prevented.

Although the stratum corneum provides great protection, it also frustrates efforts to apply beneficial agents directly to local areas of the body. The inability of physiologically active agents to penetrate the stratum corneum has resulted in a great deal of research on penetration-enhancing agents for the skin. See, for example, U.S. Pat. Nos. 3,989,815; 3,969,816; 3,991,203; 4,122,170; 4,316,893; 4,405,616; 4,415,563; 4,423,040; 4,424,210; and 4,444,762. In contrast, there has been very little research carried out on chemical agents that inhibit the penetration of toxic chemicals through the skin of mammals upon prolonged contact with mammalian skin. Toxic chemicals, such as pesticides and herbicides, can have a deleterious effect, even in the low concentrations that may diffuse through the stratum corneum under prolonged contact with mammalian skin. The need currently exists for compounds that can inhibit the passage of toxic chemicals and other bioactive agents across the stratum corneum of mammalian skin.

It is an object of the invention to provide the percutaneous absorption of toxic chemicals and other harmful agents.

It is also an object of the invention to provide topical compositions that enhance the barrier function of mammalian skin to decrease the passage of bioactive agents in either direction through the skin.

It is a further object of the invention to provide methods of inhibiting passage of bioactive agents through the skin of a mammal by applying to the skin a composition that includes a penetration-inhibiting compound.

Other objects and advantages of the instant invention will be apparent from a careful reading of the specification below.

SUMMARY OF THE INVENTION

This invention relates to novel compounds having one of Formulae I-IV that are useful for decreasing the passage of bioactive agents through mammalian skin. The invention also relates to compositions useful for inhibiting the penetration of toxic chemicals through the skin of a mammal which comprise, as a penetration inhibiting agent, at least one compound represented by one of Formulae I-IV. The invention also provides methods for inhibiting the penetration of toxic chemicals through the skin of a mammal which comprises applying to the skin a topical composition which comprises, as a penetration inhibiting agent, one or more of the compounds represented by one of Formulae I-IV.

In one embodiment, the present invention relates to novel compounds having one of Formulae I-IV.

In a second embodiment, the present invention relates to a topical compositions comprising a compound of one of Formulae I-V.

In a third embodiment, the present invention relates to a method for decreasing the percutaneous absorption of toxic chemicals through the skin of a mammal which comprises applying to the stratum corneum of the skin of a mammal in need thereof a compound having one of Formulae I-IV in an amount effective to decrease the percutaneous absorption of toxic chemicals.

In a fourth embodiment, the present invention relates to a method for increasing the stability of lipid bilayers in mammalian skin in order to decrease passage of bioactive agents through the skin of said mammal which comprises applying to the stratum corneum of the skin of a mammal in need thereof a compound having one of Formulae I-IV in an mount effective to decrease passage of bioactive gents through said lipid bilayers.

Other features and advantages of the invention will be apparent from the following description of the preferred embodiments thereof, and from the claims.

DETAILED DESCRIPTION OF THE PREFERRED EMBODIMENTS

The compounds of the present invention have one of the following Formulae:

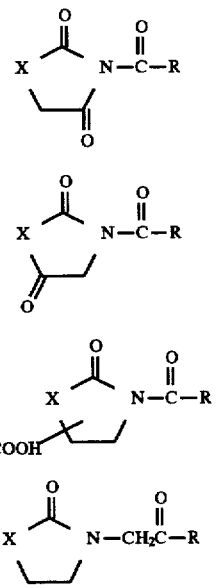

and pharmaceutically acceptable salts and esters thereof; wherein

X is one of —$CH_2$—, —NH—, —O— or —S—; and

R is a $C_{1-20}$ hydrocarbyl radical.

Preferably R is a straight or branched chain alkyl radical having from about 1 to about 20 carbon atoms, more preferably a straight chain alkyl radical having from 6 to 20 carbons. For components of Formulae I, II and III, R is most preferably —$(CH_2)_{10}$—$CH_3$. For compounds of Formulae IV, R is most preferably —$(CH_2)_9$—$CH_3$.

The compounds represented by Formulae I–IV are useful as penetration inhibiting agents. The compounds may be made by the methods described below. Typical examples of compounds of the present invention include:

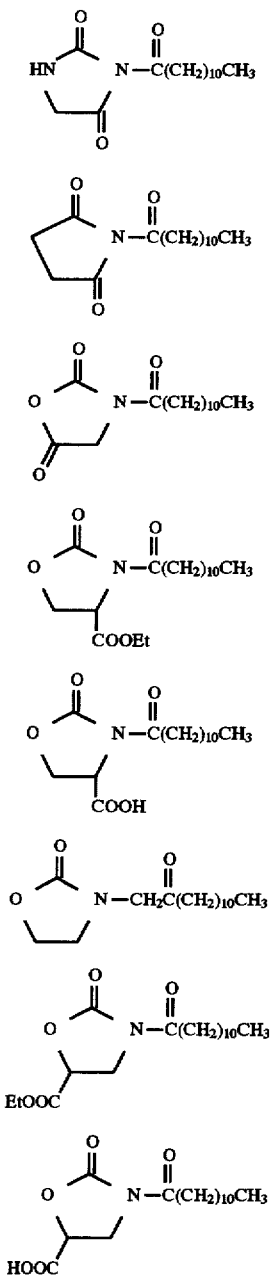

The compounds of the present invention can be employed as penetration inhibiting agents. The compounds may be formulated into topical compositions that function as barriers to the passage of bioactive compounds and agents through mammalian skin in either direction when applied to the skin. The barrier inhibits the passage of toxic chemicals from the environment through the skin into the bloodstream or underlying tissues and/or organs of the mammal. This utility is especially desirable to prevent individuals and livestock from being exposed to toxic chemicals; for example, farmers dealing with pesticides, workers cleaning up toxic waste spills and soldiers exposed to chemical weapons. The barrier may also function to prevent allergic reactions to skin products such as cosmetics and sunscreens wherein it is desired to maintain the skin product ingredients on the surface of the skin. Additionally, the barrier may function to maintain drugs utilized to treat skin conditions on the skin surface thus inhibiting penetration of the drug into the bloodstream.

For purposes of defining the invention, the term "bioactive agent" shall mean any compound capable of passage through the skin or other membrane of a mammal, having any biological effect on the mammal. The biological effect may be either desirable or undesirable.

For the purposes of defining the invention, the term "mammal" includes human beings and other forms of animal life, especially domesticated animals and pets.

The term "alkyl" as employed herein includes both straight and branched chain radicals of up to 20 carbons, preferably 6–20 carbons, such as methyl, ethyl, propyl, butyl, pentyl, hexyl, heptyl, octyl, nonyl, decyl, undecyl, dodecyl and the various branched chain isomers thereof.

Also included within the scope of the present invention are non-toxic pharmaceutically acceptable salts of the compounds of Formula I–IV. Basic salts are formed by mixing a solution of a particular compound of the present invention with a solution of a pharmaceutically acceptable non-toxic base, such as, sodium hydroxide, potassium hydroxide, sodium bicarbonate, sodium carbonate, or an amino compound, such as choline hydroxide, Tris, bis-Tris, N-methylglucamine or arginine. Water-soluble salts are preferable. Thus, suitable salts include: alkaline metal salts (sodium, potassium etc.), alkaline earth metal salts (magnesium, calcium etc.), ammonium salts and salts of pharmaceutically acceptable amines (tetramethylammonium, triethylamine, methylamine, dimethylamine, cyclopentylamine, benzylamine, phenethylamine, piperidine monoethanolamine, diethanolamine, tris(hydroxymethyl)amine, lysine, arginine and N-methyl-D-glucamine).

The compounds of the present invention may be prepared by the general procedures outlined in Schemes I through VI.

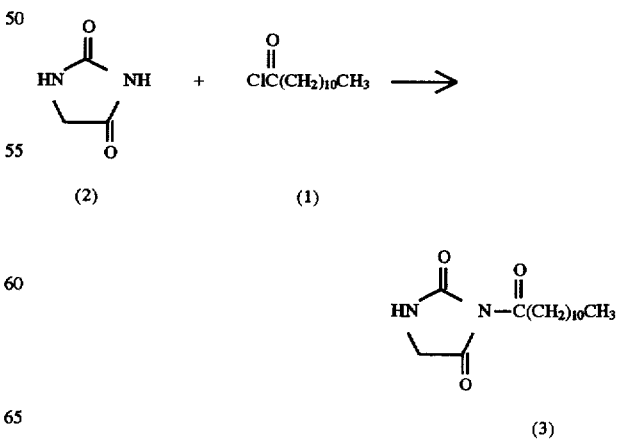

Scheme II

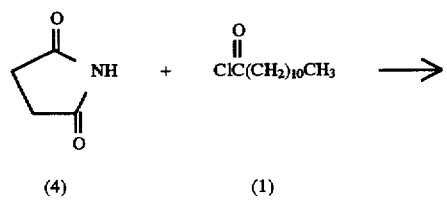

(4)  (1)

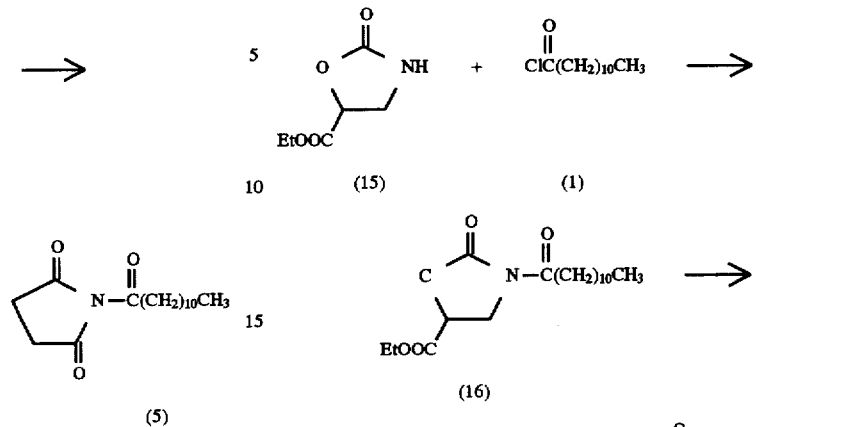

(5)

Scheme III

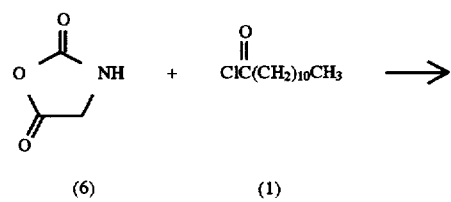

(6)  (1)

(7)

Scheme IV

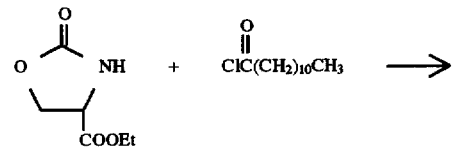

(8)  (1)

(9)

(10)

Scheme V

(15)  (1)

(16)

(17)

Scheme VI

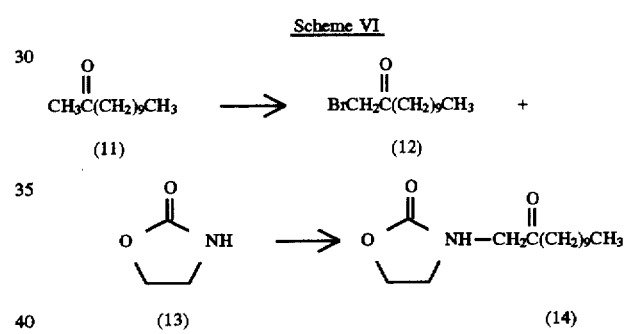

(11) (12)

(13) (14)

In each of Schemes I–V, an appropriate N-heterocyclic ketone is reacted with an acid chloride such as lauroyl chloride, decanoyl chloride or octanoyl chloride, in the presence of an organic solvent, such as toluene, and a base such as triethylamine.

In Scheme VI, a brominated ketone, such as 1-bromo-2-dodecanone is substituted for the acid chloride employed in the earlier schemes.

Dosage forms for topical application may include solution nasal sprays, lotions, ointments, creams, gels, suppositories, sprays, aerosols and the like. Typical inert carriers which make up the foregoing dosage forms include water, acetone, isopropyl alcohol, freon, ethyl alcohol, polyvinylpyrrolidone, propylene glycol, fragrances, gel-producing materials, liquid crystalline materials, mineral oil, stearyl alcohol, stearic acid, spermaceti, sorbitan monooleate, "Polysorbates," sorbitol and methyl cellulose. The preferred carriers are those in which the active ingredient is soluble. Emulsifiers, stabilizers, humectants and antioxidants may also be included as well as agents imparting color or fragrance, if desired.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water,

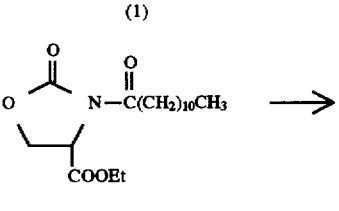

about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the active ingredient, in a suitable high molecular weight alcohol such as propylene glycol or polyethylene glycol.

The amount of the composition, and of the penetration inhibiting compound therein, to be administered will obviously be an effective amount for inhibiting penetration of a particular bioactive agent. This, of course, will be ascertained by the ordinary skill of the practitioner.

In general, the topical compositions of this invention may comprise from approximately 0.1 to 90 percent, by weight, of one or more of the compounds of Formulae I, preferably from approximately 1% to approximately 10%, and more preferably about 1% to about 5% of said compounds.

For most drugs the major barrier to penetration resides in the outer layer of the skin, the stratum corneum. The stratum corneum is an extremely impermeable membrane. The impermeability is a result of its structure and lipid composition. Macroscopically the stratum corneum is composed of dead cells (the corneocytes) and intracellular lipids forming a mortar between the corneocytes. A complex mixture of lipids are packed together to form sequences of bilayers which are responsible for the impermeability of the stratum corneum. Materials diffuse through the intracellular channels of the stratum corneum and it is the structural bilayer nature of the lipids that provides the barrier function of the skin. (Hadgraft, "Skin Penetration Enhancement," *Prediction of Percutaneous Penetration*, 3B:138–148 (1993)). While not wishing to be bound by theory, it is believed that the compounds of the present invention function by interacting with ilipid-bilayer interaction mechanism. This ability to interact with charged lipid bilayers appears to play a major role in the functioning of an entire series of penetration enhancers and the penetration barriers of the present invention.

The compounds of the present invention find particular utility in inhibiting the penetration of toxic chemicals that may come in contact with the skin of mammals. Examples of such compounds include carcinogens such as actinomycin D, arsenic compounds and DDT. It is contemplated that the compounds of the present invention can be used to inhibit the penetration of a host of carcinogens. Other exemplary carcinogens whose penetration can be inhibited are listed in the CRC Handbook of Chemistry and Physics, David R. Lide, Editor in Chief, 72nd edition (1991–1992), at Section 16, pages 32–38. Pesticides are another example of toxic chemicals whose penetration can be inhibited by the compounds of the present invention. Exemplary pesticides include organochlorine pesticides such as: aldrin, α-BHC, β-BHC, γ-BHC, δ-BHC, 4,4'-DDD, 4,4'-DDE, 4,4'-DDT, dieldrin, endosulfans, endrin, heptachlor, methoxychlor and chlordane. Other pesticides whose penetration can be blocked by compounds of the present invention include organophosphorous pesticides such as: thionazin, dimethoate, disulfoton, famphur, parathion, sulfotepp and triethylphosphorothioate. Additional toxic chemicals include hazardous compounds such as carbazoles, dibenzofurans, nitroanilines and phenols. Additionally, it is contemplated that the the penetration of insecticides such as DEET and sunscreens such as PABA can be inhibited by compounds of the present invention.

A related utility of the compounds of the present invention is the inhibition of water loss occurring by diffusion of water from inside the body through the stratum corneum.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound having one of Formulae I–IV:

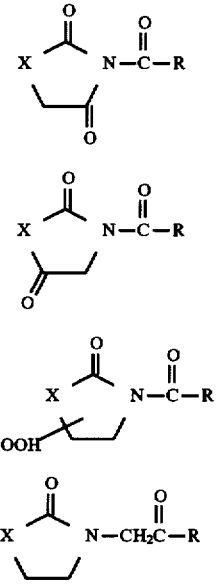

and pharmaceutically acceptable salts and esters thereof; wherein

R is a $C_{6-20}$ hydrocarbyl radical;

X is one of —$CH_2$—, —NH—, —O— or —S—.

2. The compound of claim 1, wherein R is a straight chain alkyl radical containing 6 to 20 carbon atoms.

3. The compound of claim 2 wherein R is a straight chain alkyl radical containing 10 or 11 carbon atoms.

4. The compound of claim 1 which is one of:

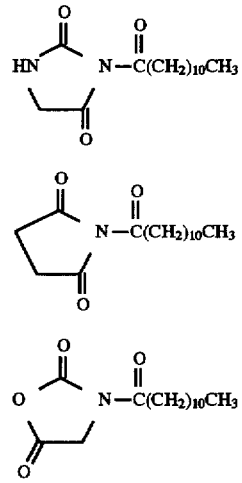

-continued

[Structure: oxazolidinone-type ring with O, C=O, N—C(=O)(CH₂)₁₀CH₃, with COOEt substituent]

[Structure: oxazolidinone-type ring with O, C=O, N—C(=O)(CH₂)₁₀CH₃, with COOH substituent]

[Structure: oxazolidinone-type ring with O, C=O, N—CH₂C(=O)(CH₂)₁₀CH₃]

[Structure: oxazolidinone-type ring with O, C=O, N—C(=O)(CH₂)₁₀CH₃, with EtOOC substituent]

-continued

[Structure: oxazolidinone-type ring with O, C=O, N—C(=O)(CH₂)₁₀CH₃, with HOOC substituent]

5. A topical pharmaceutical composition comprising a compound of claim 1 and a pharmaceutically acceptable carrier or diluent.

6. A method for decreasing the percutaneous absorption of toxic chemicals through the skin of a mammal comprising
applying to the stratum corneum of the skin of a mammal in need thereof a compound of claim 1 in an amount effective to decrease the percutaneous absorption of said toxic chemicals.

7. A method for increasing the stability of lipid bilayers in mammalian skin in order to decrease passage of bioactive agents through the skin of a mammal, said method comprising
applying to the stratum corneum of the skin of a mammal in need thereof a compound of claim 1 in an amount effective to decrease passage of bioactive agents through said lipid bilayers.

8. The method of either claim 6 or 7 wherein said mammal is a human.

9. The method of either claim 6 or 7 wherein said bioactive agent is water.

* * * * *